United States Patent [19]

Denen et al.

[11] Patent Number: 5,445,635
[45] Date of Patent: Aug. 29, 1995

[54] REGULATED-CURRENT POWER SUPPLY AND METHODS FOR RESISTIVELY-HEATED SURGICAL INSTRUMENTS

[75] Inventors: Dennis J. Denen; Albert E. Weller, both of Columbus, Ohio

[73] Assignee: Hemostatic Surgery Corporation, Grand Cayman, Cayman Islands

[21] Appl. No.: 271,388

[22] Filed: Jul. 6, 1994

Related U.S. Application Data

[63] Continuation of Ser. No. 877,454, May 1, 1992, abandoned.

[51] Int. Cl.[6] .......................... A61B 17/36; H05B 1/02
[52] U.S. Cl. ........................................ 606/27; 606/30; 606/31; 606/35; 606/42
[58] Field of Search .............. 606/27, 28, 29, 30, 606/31, 32, 33, 34, 35, 36, 37, 38, 39, 40, 41, 42, 43, 44, 45, 48, 49, 50

[56] References Cited

U.S. PATENT DOCUMENTS

| | | | |
|---|---|---|---|
| 3,730,188 | 5/1973 | Ellman | 128/303.14 |
| 4,092,986 | 6/1978 | Schneiderman | 128/303.14 |
| 4,200,104 | 4/1980 | Harris | 606/32 |
| 4,256,945 | 3/1981 | Carter et al. | 219/10.75 |
| 4,523,084 | 6/1985 | Tamura et al. | 219/497 |
| 4,549,073 | 10/1985 | Tamura et al. | 219/497 |
| 4,590,934 | 5/1986 | Malis et al. | 128/303.14 |
| 4,621,643 | 11/1986 | New, Jr. et al. | 128/633 |
| 4,626,767 | 12/1986 | Clappier et al. | 323/280 |
| 4,658,819 | 4/1987 | Harris et al. | 606/34 |
| 4,662,369 | 5/1987 | Ensslin | 128/303.13 |
| 4,700,708 | 10/1987 | New, Jr. et al. | 128/633 |
| 4,752,864 | 6/1988 | Clappier | 363/86 |
| 4,769,519 | 9/1988 | Hall | 219/10.75 |
| 4,770,179 | 9/1988 | New, Jr. et al. | 128/633 |
| 4,795,886 | 1/1989 | Carter, Jr. | 219/505 |
| 4,903,696 | 2/1990 | Stasz et al. | 606/37 |
| 4,938,761 | 7/1990 | Ensslin | 606/31 |
| 4,961,739 | 10/1990 | Thompson | 606/37 |
| 4,969,885 | 11/1990 | Farin | 606/38 |
| 5,047,025 | 9/1991 | Taylor et al. | 606/28 |
| 5,128,602 | 7/1992 | Carter, Jr. | 323/267 |

FOREIGN PATENT DOCUMENTS

| | | |
|---|---|---|
| 0209215 | 1/1987 | European Pat. Off. . |
| 3531576 | 5/1986 | Germany . |
| 51-15160 | 4/1976 | Japan . |
| 53-28399 | 8/1976 | Japan . |

*Primary Examiner*—Stephen C. Pellegrino
*Assistant Examiner*—Sonya C. Harris
*Attorney, Agent, or Firm*—Fish & Neave; Nicola A. Pisano; Victor G. Treyz

[57] ABSTRACT

A power supply for use with resistively-heated surgical instruments is provided, wherein the desired operating conditions of the surgical instrument are determined by a set-point determination circuit in combination with a set-point indicator element. The power supply includes an impedance matching circuit and current step-up transformer for reducing power loss in the cable connecting the surgical instrument to the power supply. A method of regulating the output of a power supply used with resistively-heated surgical instruments is also provided.

17 Claims, 6 Drawing Sheets

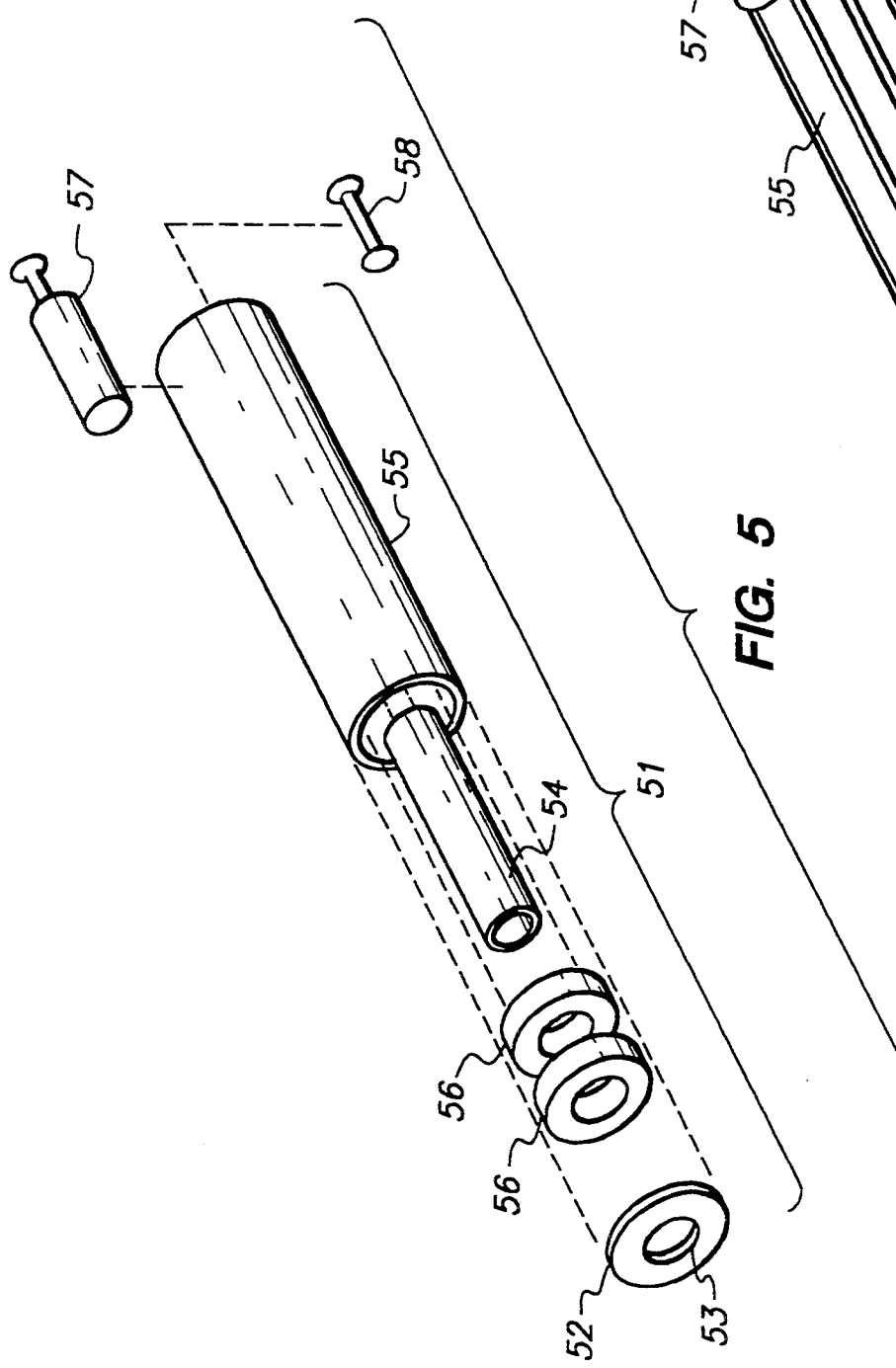
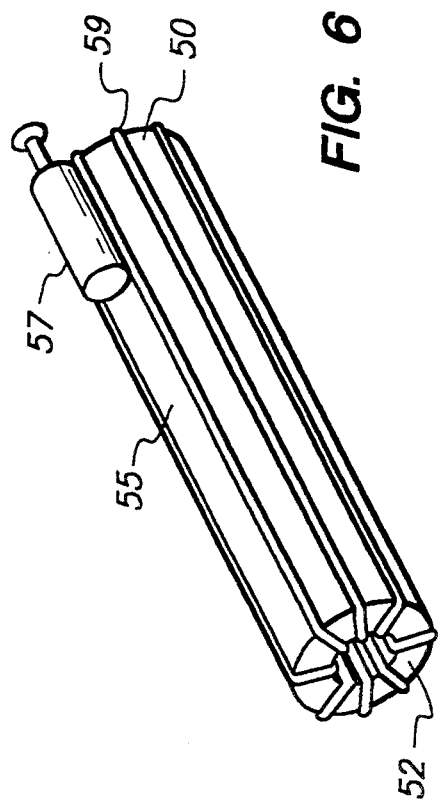
FIG. 5
FIG. 6

REGULATED-CURRENT POWER SUPPLY AND METHODS FOR RESISTIVELY-HEATED SURGICAL INSTRUMENTS

This is a continuation of application Ser. No. 07/877,454, filed May 1, 1992, now abandoned entitled REGULATED-CURRENT POWER SUPPLY AND METHODS FOR RESISTIVELY-HEATED SURGICAL INSTRUMENTS.

This invention relates to resistively-heated surgical apparatus and methods, and power supplies for operating such instruments. More particularly, this invention relates to methods and apparatus for regulating a power supply for use with surgical instruments having auto-regulating heating elements.

BACKGROUND OF THE INVENTION

The use of electrically powered surgical instruments for incising tissue and controlling bleeding therefrom is well known, as exemplified by both electrosurgical devices and resistively-heated surgical devices. In electrosurgical devices, electric current is passed directly through a patient's tissue to cut and cause hemostasis of the tissue. In contrast, in resistively-heated devices, an electric current is passed through a heating element disposed on the surgical device, thereby causing ohmic heating of the element. This thermal energy is then transferred by conduction from the surgical instrument to the patient's tissue. In either type of device, the heat deposited by the instrument facilitates cutting or hemostasis of the tissue, or both.

Some previously known resistively-heated surgical instruments generally are calibrated to provide a desired working-surface temperature in response to a selected power input. When connecting a surgical instrument to a power supply, the surgeon must take care to set the power supply controls to provide the voltages and currents specified in the manufacturer's instructions. However, due to manufacturing variability, for similar power inputs, the working-surface temperature achieved by different surgical instruments of the same type may vary. It would therefore be desirable to provide a power supply that automatically recalibrates the output supplied to the surgical instrument when the instrument is changed or replaced. Furthermore, should the instrument malfunction, it would also be desirable to provide a power supply that allows a new instrument to be connected without significant delay.

Likewise, should a surgeon need to use different types of resistively-heated surgical instruments during an operation, for example, a hook-type hemostatic probe instead of a spatula-type hemostatic probe, care must be taken to reset the controls of the power supply to reflect the different power requirements of the various instruments being used. Thus, changing instrument types may distract the surgeon's attention, and may lead to error in setting the appropriate power output for the selected surgical instrument. It would therefore be desirable that the surgeon be able to disconnect the instrument and replace it with another, with little disruption of the operation.

A drawback of previously known combinations of resistively heated surgical instruments and power supplies is the inability of the power supply to match the instantaneous power requirements of the surgical instrument as it is manipulated at the surgical site. For example, as the working-surface of the surgical instrument passes through fresh tissue, the temperature of the device may drop, thus requiring the power supply to increase the power supplied to the surgical instrument to maintain the desired working-surface temperature. As the temperature of the surgical instrument fluctuates, the thermal energy deposited by the surgical instrument in the adjacent tissue therefore also varies, and may result in uneven or ineffective hemostasis. It would therefore be desirable to provide a power supply that automatically adjusts the level of power output to the surgical instrument to effectively maintain the desired working-surface temperature.

In some previously known resistively-heated surgical instruments, heating is accomplished by applying an alternating-current (AC) voltage to a heating element. Due to the AC nature of the power supply, a mismatch of impedance between the power source and the instrument may cause undesirable loss of power. Such a mismatch is further complicated by the fact that the impedance of the heating element, and thus the instrument, can vary as the temperature of the heating element varies. This impedance mismatch may result in inefficient utilization of the power supplied by the power supply to the surgical instrument, which may be manifested as undesirable heating of the cables or the power supply. In addition, the mismatch may result in an inability of the power supply to match the instantaneous power requirements of the surgical instrument. It would therefore be desirable to provide a power supply that allows for matching of the surgical instrument to the power supply and that automatically compensates for changes in the load impedance to provide efficient transmission of power to the surgical instrument. Such a power supply would be better able to meet the instantaneous heating requirements of the surgical device.

The ability of a power supply to supply the instantaneous power requirements of the surgical instrument is also influenced by the degree of power loss in the transmission lines. Generally, the transmission of high AC current typically entails high power loss due to the resistance of the transmission medium. For example, considerable power loss may occur in the cables connecting a surgical instrument to a power source, which is manifested as ohmic heating of the cables. Alternatively, the use of bulkier cables may reduce line losses, but interferes with the surgeon's ability to manipulate the surgical instrument. It would therefore be desirable to provide a power supply for resistively-heated surgical instruments that reduces line losses in the cable connecting the components of the surgical apparatus, and that permits the use of a flexible and relatively light-weight cable.

The frequency of the alternating current applied to the surgical instrument must be such that low frequencies are not applied to the surgical instrument. In particular, leakage current at low frequencies may result in undesirable neuromuscular stimulation in the patient, which may injure the patient and interfere with the surgeon's ability to manipulate the instrument at the surgical site. Also, the frequency of the applied current also effects the extent of current leakage from the instrument to the patient, so that higher leakage is tolerable at higher frequencies. It would therefore be desirable to provide a power supply for supplying an output to a resistively-heated surgical instrument that uses high frequency alternating current.

Some resistively-heated surgical instruments may have a working-surface temperature in excess of 600° C.

in still air. Because the temperature of the working-surface of the instrument cools rapidly when contacting fresh tissue, the power supply may cause overheating of portions of the working-surface not in contact with the tissue. Wide fluctuations in temperature along the working-surface of the instrument enhance the tendency of tissue to adhere to the surgical instrument, resulting in coagulum buildup on the instrument and even tearing of adjacent tissue. It would therefore be desirable to provide a power supply that varies its output to the surgical instrument to maintain the temperature of the working-surface of the instrument in a predetermined range.

A resistively-heated surgical instrument having an auto-regulated working-surface temperature is described in co-pending and commonly-assigned U.S. patent application Ser. No. 07/986,967, filed Dec. 8, 1992. That instrument includes a working surface comprising a ferromagnetic material having a working temperature near the Curie point transition temperature of that material. As the temperature of the working surface of such a surgical instrument varies near the Curie transition temperature, the impedance of the device changes significantly. Impedance diminishes above the Curie temperature. For example, for some embodiments of the above-referenced surgical instruments, the changing impedance would support a seven or eight-fold increase in current if applied voltage is held constant as the Curie transition temperature is exceeded. This would cause a further increase in temperature, possibly resulting in thermal runaway. It would therefore be desirable to provide a power supply capable of providing a regulated current to the surgical instrument to achieve stable temperature regulation of the working-surface of the instrument.

SUMMARY OF THE INVENTION

In view of the foregoing, it is an object of the present invention to provide a power supply that automatically recalibrates the power output to the surgical instrument to reflect the particular electrical characteristics of the connected surgical instrument, and that regulates the power supplied to the instrument in accordance with that determination.

It is also an object of the present invention to provide a power supply that accepts different types of resistively-heated surgical instruments and that automatically adjusts the power output level in accordance with the specific configuration and type of the selected instrument.

It is another object of the present invention to provide a power supply including a circuit to match the impedance of the applied load, so that the power output by the power supply to the surgical instrument is efficiently utilized with little line loss. Thus, the power supply of the present invention is more responsive to the demands imposed by the resistively-heated surgical instrument.

It is a further object of the present invention to provide a power supply for use in conjunction with relatively light-weight and flexible cables to reduce power losses in the cables connecting the power supply to the surgical instrument.

It is yet another object of the present invention to provide a regulated-current power supply having a high frequency (radio frequency "RF") level that limits the quantity of current leakage to the patient.

It is an object of the present invention to provide a power supply capable of supplying a resistively-heated surgical instrument with a controlled output to maintain the working-surface temperature of an attached surgical instrument within a predetermined temperature range, so as to reduce coagulum buildup and adherence of tissue to the working-surface of the surgical instrument.

It is a further object of the present invention to provide a power supply for supplying power to a surgical instrument comprising a resistively-heated auto-regulating ferromagnetic material having a working temperature near the Curie transition point of the material, so that the power supply is capable of satisfying the power demands of the surgical instrument as its temperature varies near the Curie transition temperature.

These and other objects of the present invention are accomplished in accordance with the principles of the invention by providing a power supply having a set-point determination circuit for determining the output current level to be supplied to the surgical instrument. This circuit automatically identifies a variety of resistively-heated surgical instruments connected thereto. After identifying which instrument has been connected, the power supply automatically recalibrates and auto-regulates the delivered current in accordance with a predetermined current profile for that instrument. The set-point determination circuit may also adjust the current output responsive to the specific electrical characteristics of the surgical instrument, to account for manufacturing variability.

The power supply of the present invention includes an impedance matching circuit, to provide efficient utilization of the power output to the surgical instrument. The power supply also employs a current step-up transformer, that can be placed in the handle of the surgical instrument, that permits the use of a flexible and relatively light-weight cable for connecting the power supply to the resistively-heated surgical instrument, so as to further reduce line losses in the connecting cable.

The present invention further includes a regulated-current power supply that supplies a controlled amount of current to resistively-heated surgical instruments at a high (RF) frequency, with little current leakage. The current supplied to the instrument heats the working surface of the instrument to a temperature in the approximate range of 100° to 600° C., depending upon the type and intended application of the surgical instrument. Current delivery is regulated in order to provide a level, under varying load conditions, sufficient to maintain the working surface temperature near a predetermined working temperature.

The present invention also includes methods of using a regulated-current power supply in conjunction with a surgical instrument having an auto-regulating heating element, so that the power supplied to the surgical instrument throughout the phases of operation of the device maintains the working surface of the surgical instrument near a predetermined working temperature.

BRIEF DESCRIPTION OF THE DRAWINGS

The above and other objects and advantages of the present invention will be apparent upon consideration of the following detailed description, taken in conjunction with accompanying drawings, in which like reference characters refer to like parts throughout, and in which:

FIG. 5 is an exploded perspective view of the secondary winding of a current step-up transformer constructed in accordance with the principles of the present invention;

FIG. 6 is a perspective view of the current step-up transformer of FIG. 5;

DETAILED DESCRIPTION OF THE PREFERRED EMBODIMENTS

Figure 1:
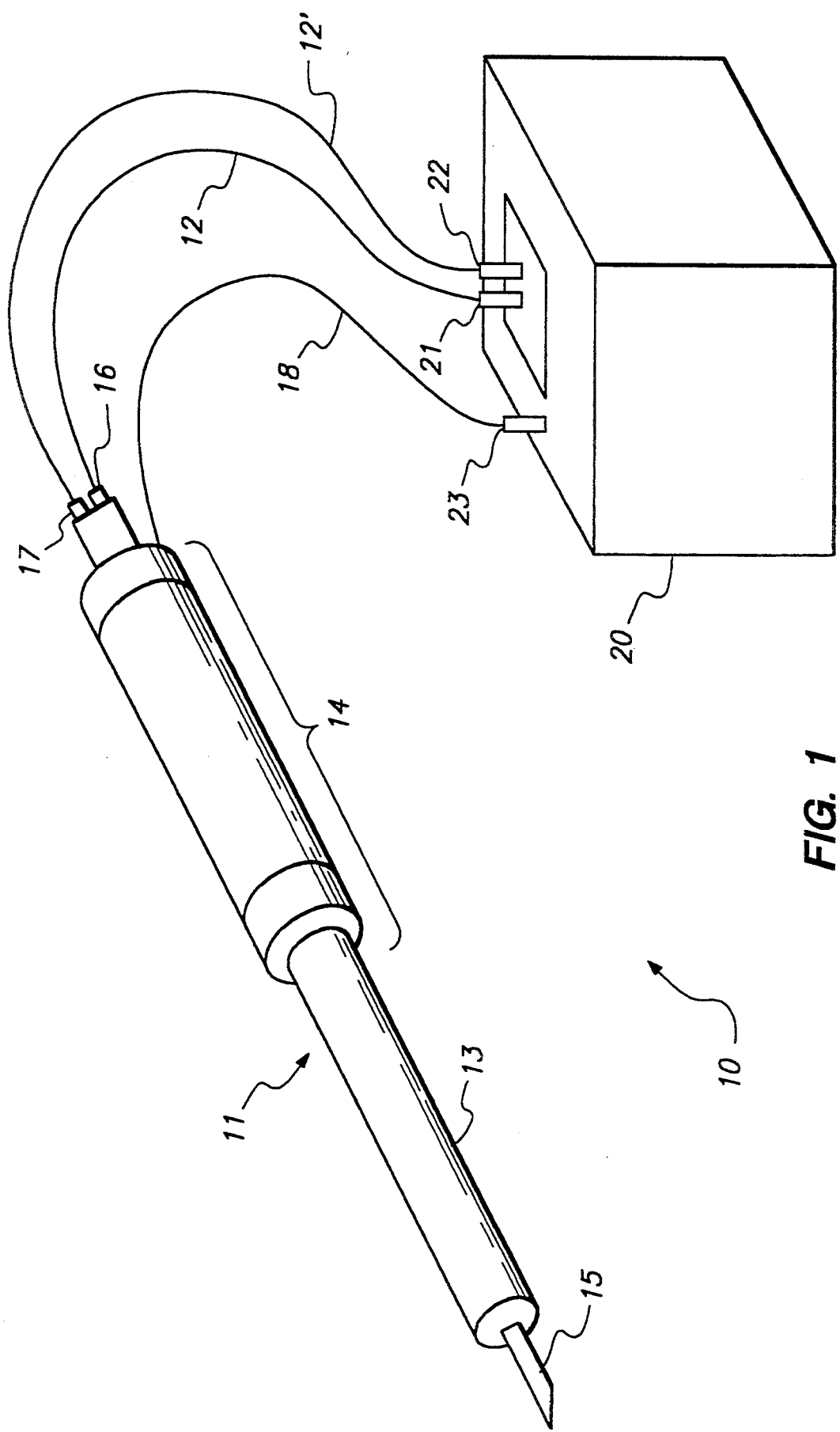
FIG. 1 is a perspective view of a power supply and surgical instrument constructed in accordance with the principles of the present invention.

Referring to FIG. 1, resistively-heated surgical apparatus 10 is described. Apparatus 10 includes surgical instrument 11 controlled and powered by power supply 20. Surgical instrument 11 may be any type of resistively-heated surgical instrument powered by an alternating current (AC), although for the illustrative embodiments discussed hereinafter, the surgical instrument employs a resistively-heated heating element that exhibits auto-regulating behavior. For example, surgical instrument 11 may be an auto-regulating temperature scalpel, such as that described in Shaw U.S. Pat. No. 4,185,632, or an endoscopic instrument, such as that described in above-mentioned U.S. patent application Ser. No. 07/986,967, filed Dec. 8, 1992.

Instrument 11 typically includes handle 14 having heating element 15 disposed from the distal end of a shaft 13, and terminals 16 and 17 for accepting connecting cables 12 and 12'. Power supply 20 supplies alternating current (AC) power to heating element 15. Depending upon the composition and intended use of the surgical instrument, heating element 15 may achieve a working temperature selected from the range of about 100° C. to 600° C.

Figure 2:
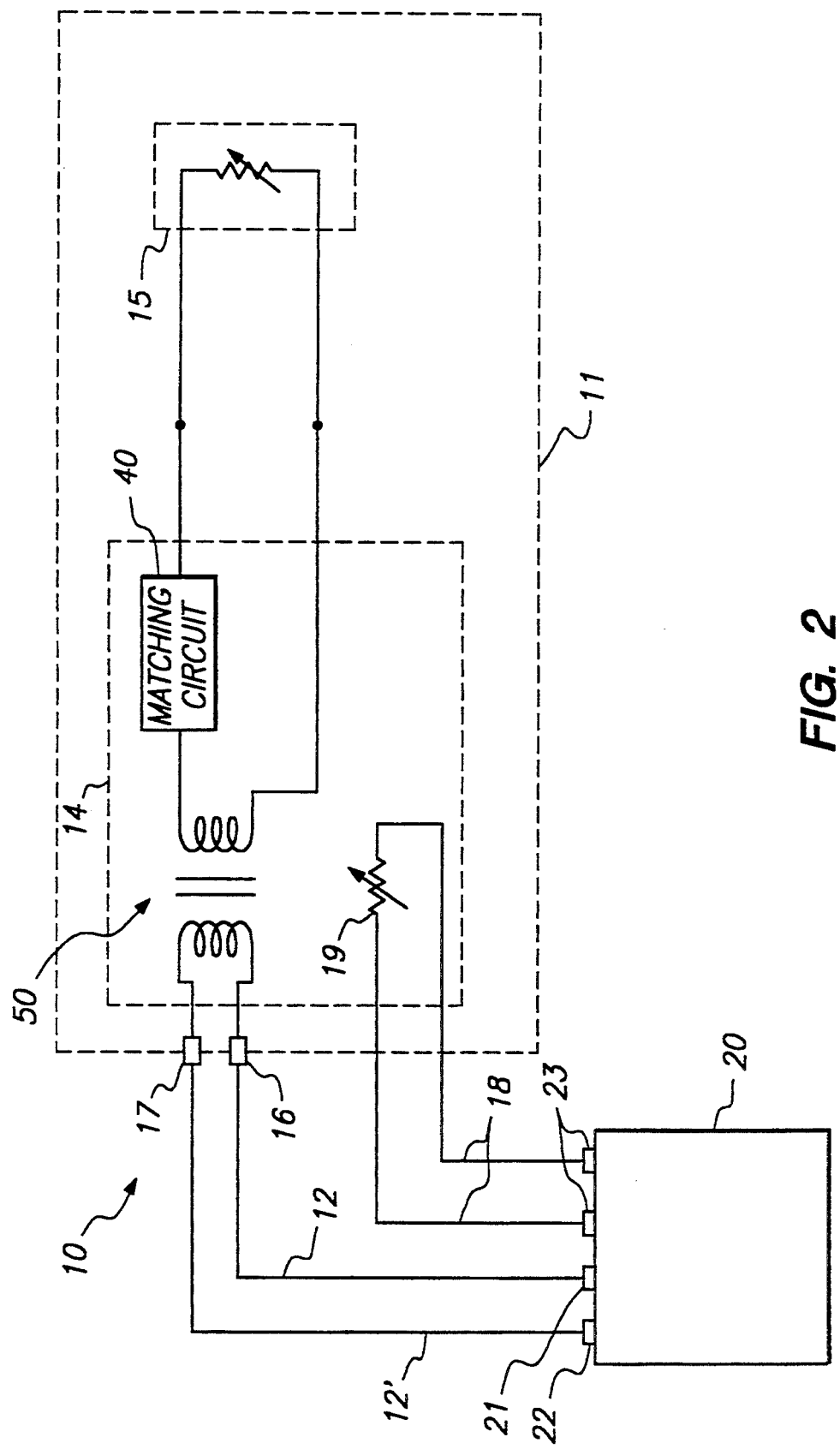
FIG. 2 is a schematic block diagram of the apparatus of FIG. 1.
Figure 3:
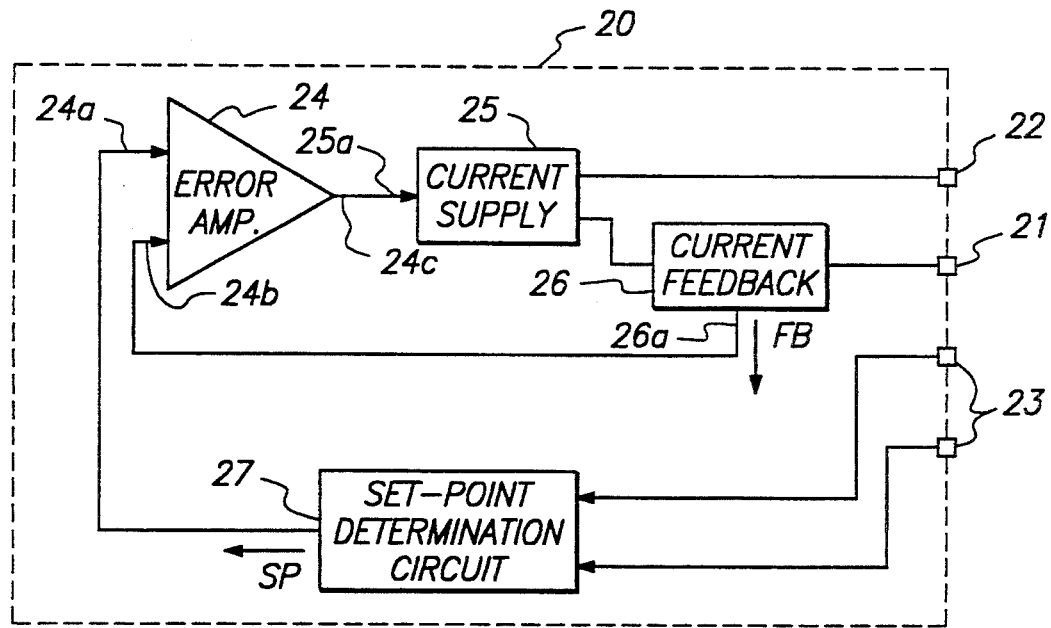
FIG. 3 is a schematic block diagram of a first embodiment of the power supply of the present invention.

Referring to FIGS. 1–3, a first embodiment of the power supply of the present invention is described. Surgical instrument 11 includes set-point indicator element 19, matching circuit 40 and current step-up transformer 50 in handle 14. Matching circuit 40 and current step-up transformer 50 will be discussed in greater detail below. These components transfer the AC power delivered from power supply 20 through cables 12 and 12' to heating element 15 of surgical instrument 11.

Set-point indicator element 19 in handle 14 enables power supply 20 to automatically determine the type of surgical instrument connected thereto. Thus, power supply 20 is able to supply power to surgical instrument 11 without the need for a surgeon to manually turn a dial on the control panel (not shown) of power supply 20 to indicate the type of surgical instrument connected thereto and the particular power supply requirements needed for performing surgery.

Set-point indicator element 19 may be, for example, a factory-preset variable resistor having a resistance value corresponding to a predetermined type of heating element with predetermined power supply requirements, i.e., voltage and current output levels. For example, for a scalpel that operates at a temperature of 250° C., the resistor may be set at the factory to a first value (e.g., 250 ohms) corresponding to the current required to maintain the scalpel at that temperature (e.g., 1.25 amps), while for a scalpel that operates at a temperature of 600° C., the resistor may be set to second value (e.g., 600 ohms) indicating a higher current level (e.g., 3.0 amps).

Referring particularly to FIG. 3, a schematic diagram of a first embodiment of power supply 20 is described. Power supply 20 includes error amplifier 24, current supply circuit 25, current feedback circuit 26, and set-point determination circuit 27. Power supply 20 works as follows.

In accordance with the present invention, set-point determination circuit 27 detects the resistance of set-point indicator element 19 (by, for example, applying a constant current or constant voltage, and measuring the resulting voltage or current, respectively) and supplies a set-point signal SP corresponding to the appropriate desired operating current level of the surgical instrument. Set-point signal SP is applied to an input terminal 24a of error amplifier 24, which in turn controls current supply circuit 25 through control terminal 25a. Current supply circuit 25 supplies an output current between output terminals 21 and 22 in response to the control signal at control terminal 25a.

Feedback circuit 26 monitors the output current of current supply circuit 25 and provides a feedback signal FB corresponding to that current at feedback terminal 26a. The feedback signal FB is then coupled to input terminal 24b of error amplifier 24. Error amplifier 24 compares the feedback signal FB received from feedback control terminal 26a to the set-point signal SP received from set-point determination circuit 27, and provides a control signal at output terminal 24c which corresponds to the difference between the desired set-point signal SP and the feedback signal FB. Circuit 20 operates to maintain the feedback signal FB at the same level as the set-point signal SP.

Current supply circuit 25 is controlled by output 24c of error amplifier 24 which adjusts the output current until the difference between the feedback signal FB and the set-point signal SP approaches zero. Thus, the current supplied by power supply 20 is automatically regulated to a constant current level set by set-point indicator element 19 in the handle 14 of surgical instrument 11 without the need for a surgeon to manually set the desired operating current level of the surgical instrument.

As discussed above, set-point determination circuit 27 is used in combination with set-point indicator element 19 to automatically provide information (i.e., desired operating current) about the surgical instrument which is connected to the power supply. In accordance with another feature of the present invention, set-point determination circuit 27 may, in the alternative, be a microprocessor that communicates with a corresponding memory device incorporated in the handle of the surgical instrument, such as that described in concurrently filed, copending and commonly-assigned U.S. patent application Ser. No. 07/986,967, filed Dec. 8, 1992. For this embodiment of the present invention, digital signals would be used to determine the type of instrument connected thereto and corresponding power requirements.

Figure 4:
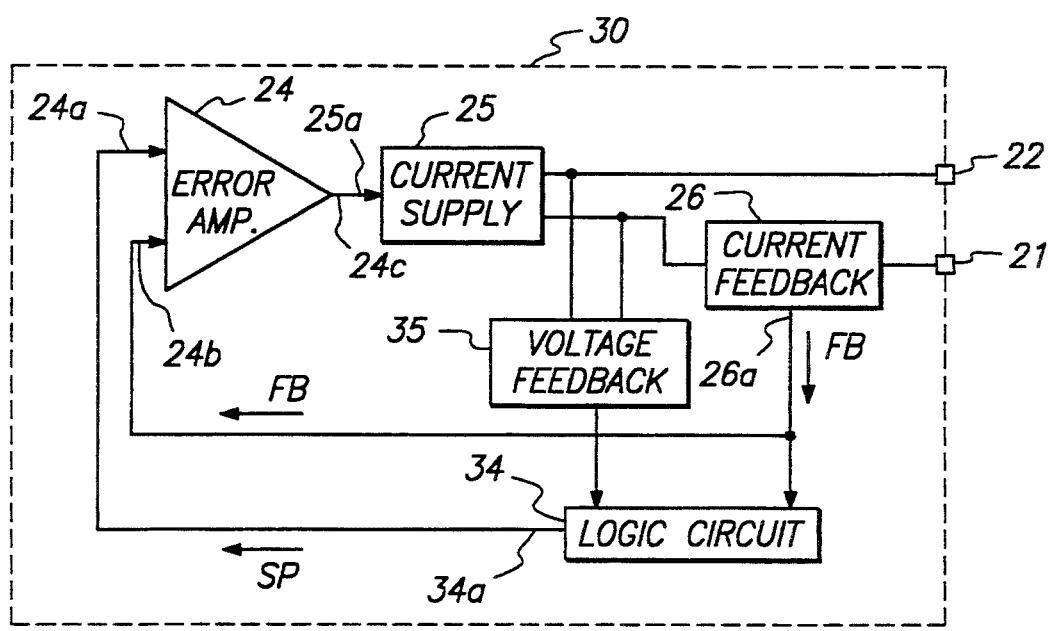
FIG. 4 is a schematic block diagram of an alternative embodiment of the power supply of the present invention.

In FIG. 4, an alternative embodiment 30 of power supply 20 is described. In contrast to the embodiment of power supply 20 shown in FIGS. 1–3, power supply 30 includes additional circuitry which is capable of determining the type of surgical instrument connected to the power supply by monitoring that instrument's current-voltage characteristics (i.e., either current or voltage values, or a combination thereof). This feature of the present invention eliminates the need for including a set-point indicator element in the handle of the surgical instrument. Furthermore, this additional circuitry allows power supply 30 to provide improved current regulation, and thus temperature stability, for resistively-heated heating elements in surgical instruments.

Power supply 30 shown in FIG. 4 has particular application for surgical instruments that employ a heating element made of a material that exhibits a Curie transition in electrical characteristics so as to allow auto-regulation of the heating element temperature. As described in copending, concurrently filed and commonly assigned U.S. patent application Ser. No. 07/986,967, filed Dec. 8, 1992, the specification of which is hereby incorporated by reference, the auto-regulating temperature feature of these particular types of heating elements results from a Curie transition in current conduction properties as the temperature of the heating element varies. Such materials exhibit a "skin depth" effect, wherein alternating current is confined to a region adjacent to the surface of the material. The current density is generally greatest at the surface and decreases in magnitude further into the material where the electric field approaches zero.

In accordance with the present invention, operation of such auto-regulating heating elements may be generally described as follows. A current level sufficient to heat the heating element to a temperature above its Curie point is applied, so that current flows through a substantial portion of the cross-section of the heating element. When the working surface of the heating element contacts moist tissue, the temperature of the heating element cools below the Curie transition point. In response, the local skin depth decreases, reducing the conductance of the material in that region and accordingly increasing the power dissipation ($I^2R$ heating) in that region. Consequently, for a substantially constant current applied to the heating element, the increased power dissipation caused by the reduction in the skin depth of the locally cooled region of the heating element therefore tends to increase the temperature of that region back above the Curie point. The temperature of the working-surface of the heating element is thus maintained near its predetermined auto-regulation temperature, i.e., near the Curie transition point temperature.

Although the present embodiment of power supply 30 will be discussed with reference to auto-regulating heating elements, it is to be understood that the present invention could also be used to power other types of resistively-heated surgical instruments. Power supply 30 works as follows.

Analogously to power supply 20 shown in FIGS. 1–3, power supply 30 includes error amplifier 24, current supply circuit 25 and current feedback circuit 26. In contrast, however, power supply 30 further includes adaptive logic circuit 34 and voltage feedback circuit 35, which are used to intelligently control the amount of AC current that current supply circuit 25 delivers to a surgical instrument coupled to terminals 21 and 22 of the power supply.

Voltage feedback circuit 35 and current feedback circuit 26 monitor the voltage and current characteristics, respectively, delivered by the power supply. Adaptive logic circuit 34, which may be implemented using analog circuitry or digital circuitry (e.g., a microprocessor), sets the current drive characteristics of the power supply 30 by comparing actual current and voltage characteristics to the desired predetermined characteristics. In accordance with the present invention, adaptive logic circuit 34 is used to generate a set-point signal SP and supply it to input terminal 24a of error amplifier 24. Power supply 30 maintains the current feedback signal FB from current feedback terminal 26a, at a value substantially equivalent to the set-point signal SP.

The initial current supplied by power supply 30 is determined and set by adaptive logic circuit 34. The resistance of heating element 15, which is initially a high value for auto-regulating heating elements, substantially decreases (by as much as 700 percent) when the Curie point temperature of the heating element material is exceeded. Monitoring the current or voltage reflected off the transmission line cable connected to the heating element (i.e., connecting cables 12 and 12'), while the heating element is heating up, allows the Curie transition to be simultaneously detected by adaptive logic circuit 34.

Adaptive logic circuit 34 monitors the signals from current feedback circuit 33 and voltage feedback circuit 35. These signals are then used to determine the variation in the current-voltage characteristics of the heating element as it heats up. The current-voltage characteristics are indicative of the resistance of the heater element. After initial heat-up, when the resistance of the heating element decreases due to the Curie transition and the temperature is slightly above the auto-regulation temperature, a second lower value of current is then chosen by adaptive logic circuit 34 so that the temperature of the heating element will fall below the auto-regulation temperature if the power supply is maintained at the lower current level. Power supply 20 then provides current regulation by responsively cycling between the high and low current values as needed in order to maintain the temperature of the heating element near its auto-regulation temperature.

When no thermal load is imposed on the surgical instrument, the power supply spends a substantial majority of its cycle time at the lower current level since it does not take much time at the higher current level to heat the heating element to a temperature in excess of the auto-regulation temperature. In contrast, when there is a thermal load on the surgical instrument, e.g., when the surgical instrument is in contact with cold tissue, the power supply spends a larger portion of its cycle time at the higher current level, since more power is required to heat a thermally-loaded heating element to its auto-regulation temperature.

If logic circuit 34 is implemented using analog circuitry, it is preferable that once the high and low current values are chosen, that they remain the same during further operation of a given surgical instrument. In other words, after adaptive logic circuit 34 determines the current level and corresponding set-point signal SP necessary to keep the heating element at a predetermined temperature below its auto-regulation temperature in still air, a second higher current and set-point signal SP are chosen corresponding to the amount of heat necessary to maintain the temperature of the heating element near its auto-regulation temperature when the heating element is thermally loaded. Temperature regulation of instrument 11 is obtained by cycling between these two current levels and their corresponding set-point signals.

For example, when the working surface of the surgical instrument is exposed to still air, the initial application of current will quickly raise the temperature of the heating element above the Curie point transition temperature. High and low current levels are established that are capable of maintaining the temperature of the heating element at its auto-regulation temperature by responsively cycling between the established current levels. If the working surface of the heating element is then brought into contact with colder moist tissue, the temperature of the working surface falls causing an increase in the resistance of the heating element, and thus a change in its corresponding current-voltage characteristics. Adaptive logic circuit 34 monitors this increase in resistance, which is reflected in the current and voltage characteristics of the heating element, and causes the power supply to operate at the higher current level to drive the working surface temperature to its corresponding auto-regulation temperature. As long as the thermal load imposed on the working surface remains relatively constant, the cycle rate between high and low current values will remain substantially constant. This scheme ensures that the power supplied to the heating element matches the instantaneous power requirements of the surgical instrument, while reducing the likelihood that the heating element will be damaged by the application of needlessly high current levels.

In an alternative microprocessor or digital circuitry-based embodiment of logic circuit 34, power supply 30 preferably cycles the temperature of instrument 11 above and below the auto-regulation temperature in order to more accurately "learn" the auto-regulation current necessary to keep the heating element at its corresponding auto-regulation temperature in still air. In accordance with this feature of the present invention, the low current value discussed above is progressively increased until a current level is established at which point the temperature of the heating element is maintained at a temperature slightly above its auto-regulation temperature with no thermal load imposed on the surgical instrument. Thus, for this particular embodiment of the present invention, adaptive logic circuit 34 automatically determines the set-point signal SP necessary to maintain the heating element at a temperature slightly higher than its auto-regulation temperature in still air.

Once a set-point signal SP is established to maintain the temperature of the unloaded heating element slightly above its auto-regulation temperature, a second set-point signal is applied to raise the temperature of the heating element when a thermal load is imposed on the surgical instrument. Thus, for this particular embodiment of the present invention, the lower current level is used to maintain the heating element at a temperature slightly above the auto-regulation temperature in still air, without the need for power supply oscillation, while a higher current level is chosen to provide enhanced current capabilities when a thermal load is imposed on the surgical instrument. Under loading conditions, cycling between the high and low current levels is used to provide current and temperature regulation.

Whichever type of adaptive logic circuit is employed (i.e., whether or not current "oscillation" is used to heat the heating element when no thermal load is imposed on the heating element), the regulation scheme of power supply 30 shown in FIG. 4 automatically determines the current conditions to maintain the heating element at its auto-regulation temperature. This feature of the present invention eliminates the need for providing a set-point indicator element in the handle of the surgical instrument or for manually setting a dial on a control of the power supply. The regulation scheme further eliminates the need for factory calibration of the surgical instrument (i.e., the setting of a resistor corresponding to the optimum operating current) and also accounts for manufacturing variability between different instruments of the same type.

Referring again to FIG. 2, the power supply of the present invention also provides a matching circuit 40 that matches the impedance of the resistively-heated surgical instrument to that required by power supply 20, to provide for efficient transmission of power therebetween. Matching circuit 40 is coupled, preferably in series, between current step-up transformer 50 and heating element 15 of surgical instrument 11 and may comprise, for example, a conventional capacitive or inductive circuit or combination thereof.

For the embodiments of the present invention contemplated by the applicants for use with an auto-regulating heating element, power supply 20 employs high frequencies in the range of about 400 kHz to 8 MHz. At such frequencies, heating element 15 of instrument 11 and connecting cables 12 and 12' behave like distributed capacitance and inductance elements along a transmission line. For example, typical inductive loads associated with current step-up transformer 50 and cables 12 and 12' cause losses in output voltage, and therefore reduce the power delivered to heating element 15. Also, AC power supplied by power supply 20 to surgical instrument 11 via cables 12 and 12' may be partially reflected back from heating element 15 if an impedance mismatch exists. Moreover, the power inefficiencies caused by an impedance mismatch may require larger currents to be delivered by the power supply to obtain the desired power dissipation in heating element 15.

Impedance matching circuit 40 therefore comprises a single series resonance capacitor, or a series of capacitors and inductors, which provide an impedance match to that of the power supply and interconnecting cables. Matching circuit 40 thereby provides efficient power transmission to heating element 15 of surgical instrument 11. Because matching circuit 40 tunes out the effect of the capacitances and inductances associated with connecting cables 12 and 12' and surgical instrument 11, the power loss in components other than heating element 15 is kept small. By way of illustration, for a surgical instrument requiring 25 watts to heat heating element 15 to its auto-regulation temperature, power supply 20 producing 5 amperes, and additional impedances causing a 10 volt drop in the output voltage, power supply 20 must produce 75 watts of power. By inserting matching circuit 40 between the power supply and the heating element, in this case a capacitor of approximately 0.03 microfarad, the 10 volt drop is compensated for and power supply 20 need only supply slightly more than 25 watts to achieve proper heating of heating element 15.

As would be apparent to one skilled in the art, the matching circuit of the present invention could also be coupled to the input winding of current step-up transformer 50 instead of the output winding as shown in FIG. 2. Additionally, the matching circuit of the present invention could also be coupled to heating element 15 in a region adjacent the heating element instead of in the handle of the surgical instrument.

To further improve the efficiency of power transmission from power supply 20 to heating element 15 of surgical instrument 11, the apparatus of the present invention includes a current step-up transformer 50 located in handle 14 of surgical instrument 11, and lightweight, flexible connecting cables 12 and 12'. In a typical application, cables 12 and 12' may be 10 feet long, thus power loss along the cable may be significant. Since power loss in the connecting cables is proportional to the square of the current supplied by power supply 20, applicants determined that power could be more efficiently supplied to the surgical instrument using higher voltages and lower currents than those actually required by heating element 15. Accordingly, power is supplied via connecting cables 12 and 12' to surgical instrument 11 at a root-mean-square (RMS) current level below that desired to achieve the working temperature of the heating element. Current step-up transformer 50 then converts the supplied voltage and current to a higher-current, lower-voltage output, which is applied to heating element 15.

Not only does the use of the current step-up transformer of the present invention improve the efficiency of the power supply, but it also permits the use of lighter, smaller diameter cables 12 and 12', than would otherwise be possible. For example, cables 12 and 12' may be constructed of Litz wire, which has a low resistance and permits the transmission of medium level current with little power dissipation. Consequently, connecting cables 12 and 12' are less likely to interfere with maneuverability of the surgical instrument, and the combination of current step-up transformer 50 and cables 12 and 12' provides a compact, lightweight and highly maneuverable instrument.

Referring now to FIGS. 5 and 6, current step-up transformer 50 of the present invention is described. Step-up transformer 50 increases approximately eightfold the current supplied by power supply 20 via connecting cables 12 and 12'. This increase is achieved by employing a miniature, lightweight, single-turn secondary winding. Secondary winding 51 of current step-up transformer 50 comprises washer 52 having aperture 53, inner tube 54 and outer tube 55 that is substantially cylindrical. The "core" of the transformer is composed of a plurality of toroids 56. Each toroid 56 comprises a doughnut-shaped piece of ferromagnetic material coated with an electrically-insulating material. The toroids provide a magnetic contribution to the step-up transformer, while the insulating coating provides electrical isolation.

Inner tube 54 and outer tube 55 are affixed to washer 52 so that inner tube 54 aligns with aperture 53. Outer tube 55 is engaged to the periphery of washer 52. Toroids 56 are dimensioned to fit into the annulus between inner tube 54 and outer tube 55. The toroids are secured within assembly 51 by suitable means, for example, by crimping the end of outer tube 55. Components 52, 54, and 55 are constructed of a conductive metal or alloy, for example copper, and may be assembled using conventional soldering or crimping techniques.

A matching circuit element, sized to match the impedance of surgical instrument 11 to power supply 20 and connecting cables 12 and 12', comprises series resonance capacitor 57 mounted to the exterior of outer tube 55. Capacitor 57 provides one of the output terminals of current step-up transformer. Lead 58 is attached to the interior of inner tube 54 in a position diametrically opposed to capacitor 57 to provide the other output terminal of the transformer.

As shown in FIG. 6, the primary winding of current step-up transformer 50 is formed by a plurality of windings 59, preferably eight to achieve the desired 8:1 increase in current. Windings 59 are wound at equi-angular spacing from end-to-end on assembly 51, so that they extend along the exterior of outer tube 55 and return along the interior of inner tube 54. The resulting lightweight, high power transformer of the present invention is therefore sufficiently compact to be inserted within the handle of a resistively-heated surgical instrument. Although the embodiment of transformer 50 shown in FIG. 6 is substantially cylindrical, those skilled in the art will realize that other shapes could as well be employed.

The power supply of the present invention in combination with current step-up transformer 50 together deliver high power at high current and low voltage to the resistively-heated surgical instrument. Additionally, the power supply of the present invention delivers high power at a frequency that reduces the likelihood of causing undesirable neuromuscular stimulation during surgery. The use of high frequency current, preferably 1.8 MHz, also reduces the risks associated with leakage current.

Figure 7:
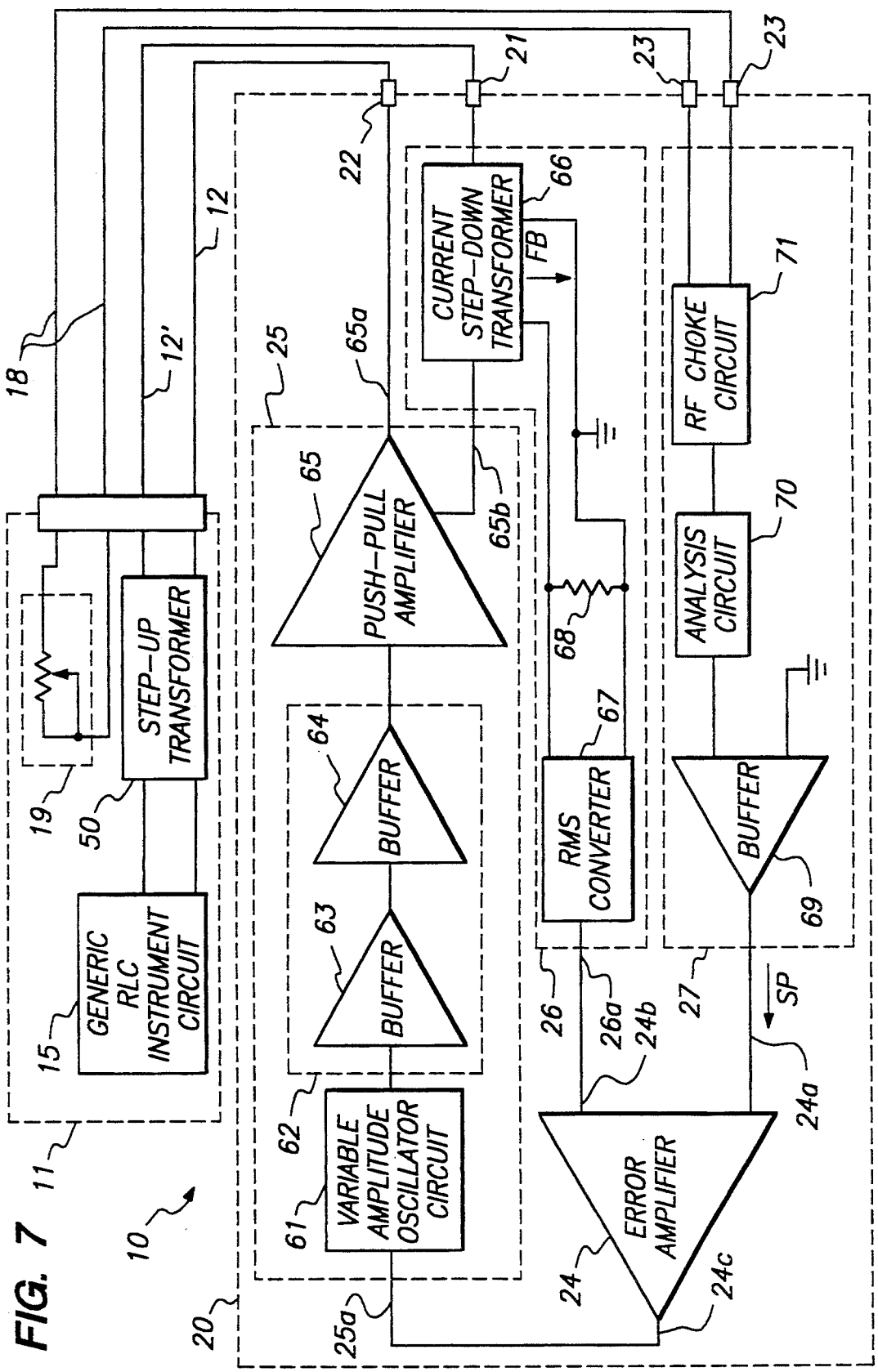
FIG. 7 is a detailed block diagram of the power supply of FIGS. 1–3.

Referring now to FIG. 7, a detailed block diagram of a preferred embodiment of regulated-current power supply 20 corresponding to that of FIG. 3 is described. Current supply circuit 25 comprises variable oscillator circuit 61, buffer circuit 62 and push-pull amplifier 65. Variable amplitude oscillator circuit 61 has an oscillator (not shown) that generates a sine wave with a frequency of approximately 1.8 Mhz and a peak-to-peak voltage output of 0-150 volts at 0-100 milliamperes of current. The sine wave is passed through a step-down transformer (an internal element of oscillator circuit 61), having a ratio of approximately 5:1, that reduces the final output voltage of oscillator circuit 61 to a typical peak-to-peak output of 0-30 volts. As will of course be recognized by one skilled in the art, the output current of the oscillator is unaffected by the step-down transformer.

Buffer circuit 62, which is connected to the output of oscillator circuit 61, performs decoupling and amplification functions for the power supply. Buffer circuit 62 comprises isolation buffer 63 and power buffer 64. Buffer 63 decouples oscillator circuit 61 from the downstream circuitry so that spurious frequencies are not propagated in the balance of the device. Buffer 63 may reduce the current flow to a range of about 0-20 milliamperes, with no change in voltage. The output of buffer 63 is supplied to buffer 64. Buffer 64 maintains a voltage level of 0-30 volts, while amplifying the current output to a range of about 0-500 milliamperes.

The output signal of power buffer 64 is fed to push-pull amplifier 65, which provides the final stage of power amplification for current supply circuit 25. The output signal of push-pull amplifier 65 also maintains a voltage range of 0-30 volts, but increases the current to a range of about 0-3.5 Amperes, thereby providing a potential power output of approximately 100 watts. The output of push-pull amplifier 65 is connected to terminal 22 to enable a variety of resistively-heated surgical instruments to be driven by the power supply.

As described heretofore, resistively-heated surgical instrument 11 includes a set-point indicator element 19. Set-point indicator element 19 is connected to set-point determination circuit 27 via lines 18 and terminals 23. Determination circuit 27 comprises RF choke circuit 71, analysis circuit 70, and buffer 69. RF choke circuit 71, which receives input signals from terminals 23, isolates the RF energy in surgical instrument 11 from analysis circuit 70 by separating the direct current (DC) components from the RF signal. The DC components are passed to analysis circuit 70 where the resistance of set-point indicator element 19 is evaluated, as described heretofore. Once the type of surgical instrument 11 has been identified, set-point determination circuit 27 establishes the set-point signal SP for the operation of instrument 11 and passes the set-point signal SP to input 24a of error amplifier 24 through buffer 69.

Current feedback circuit 26 includes current step-down transformer 66, burden resistor 68, and RMS converter 67. Step-down transformer 66 is coupled to the return line 12' of instrument 11 and provides a 20:1 step-down of the current through heating element 15, which may comprise resistive, inductive and capacitive loads. Burden resistor 68 is coupled across the output of current step-down transformer 66 to provide a conversion from a current value to a corresponding voltage value. This voltage value is passed to RMS converter 67 which provides a DC current feedback signal FB corresponding to the current level through heating element 15. This feedback signal FB is passed to input 24b of error amplifier 24. Error amplifier 24, in turn, provides an input signal to oscillator circuit 61 proportional to the difference between feedback signal FB and set-point signal SP. As discussed above, power supply 20 works to maintain the feedback signal FB at substantially the same level as the set-point signal SP.

Figure 8:
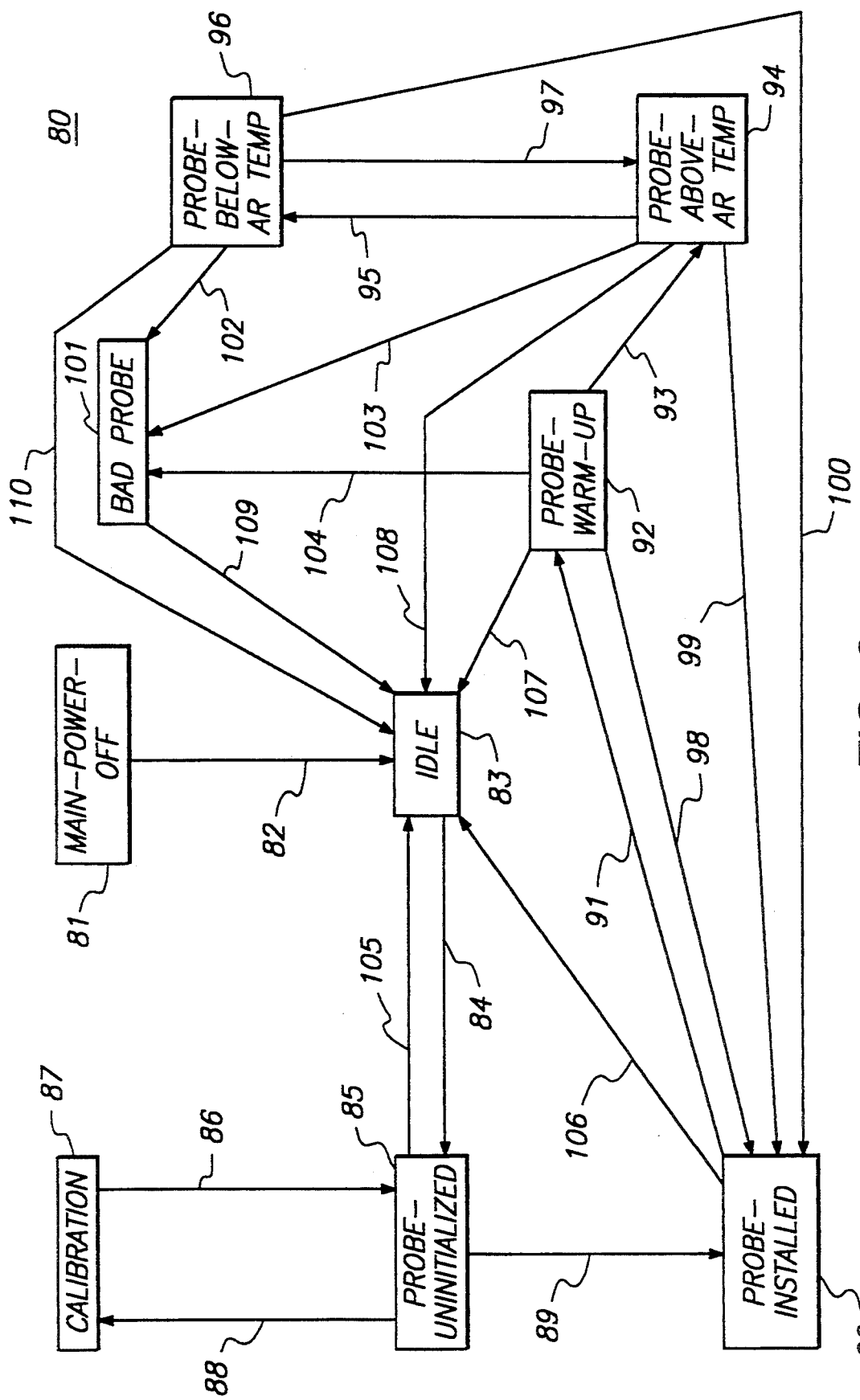
FIG. 8 is a state diagram illustrating a method of operating a resistively-heated surgical instrument in accordance with the present invention.

Referring now to FIGS. 1 and 8, state diagram 80 illustrates a method of operating a resistively-heated surgical apparatus. For purposes of illustration, state diagram 80 contemplates a surgical instrument comprising a probe, which may be energized either by a switch contained in the instrument handle or an optional foot-activation pedal connected to the power supply.

Main-power-on 81 is the initial state of the power supply. Once the "on-off" switch on the power supply console has been turned on, power-on condition 82 transfers control to idle state 83. The power supply remains in idle state 83 until the resistively-heated surgical instrument is connected to it. Connection of a surgical instrument to the power supply, condition 84, transfers control to probe-initialization state 85. If calibration-done condition 86 is false, calibration-request condition 88 causes transfer of control to calibration state 87 where the power supply determines which type of instrument has been connected to the power supply. Once calibration-done condition 86 is true, control transfers control via probe-initialized condition 89 to probe-installed state 90, and instrument is ready for use.

When the surgical instrument is energized, either by the handle switch or foot pedal, control transfers through energize condition 91 to probe-warm-up state 92, and current is applied to the heating element of the surgical instrument. The above-described feedback circuits monitor the current-voltage characteristics of the heating element, which are indicative of the resistance of the heating element, until they signify that heating element 15 has exceeded its auto-regulation temperature (i.e., heating element resistance is low). Upon the occurrence of this resistance-low condition 93, control transfers to probe-above-auto-regulation temperature state 94.

The power supply then reduces the supply current, causing the heating element to cool. When the temperature drops below the auto-regulation temperature, an increase in resistance is detected, resistance-high condition 95, and control transfers to probe-below-auto-regulation temperature state 96. The power supply thereafter cycles between states 96 and 94 via state transitions resistance-low 97 and resistance-high 95 to maintain the heating element at its auto-regulated temperature. If the surgical instrument is de-energized via the handle switch or foot pedal, control immediately transfers back to probe-installed state 90, via de-energize conditions 98, 99, or 100.

State diagram 80 also shows the response of the power supply to faults created by a malfunctioning heating element, bad-probe state 101. If an open-circuit or short-circuit is detected in the surgical instrument after probe-installed state 90 is achieved, control transfers immediately to bad probe state 101, which causes shut-down of the power supplied to the surgical instrument. Transfer of control in this manner occurs upon the occurrence of probe-open/short conditions 102, 103, or 104. Additionally, whenever the surgical instrument is disconnected, control transfers immediately to idle states 83 via handle-removed conditions 105, 106, 107, 108, 109, or 110.

The present invention therefore provides a method of operating a power supply that supplies power at predetermined levels to a resistively-heated surgical instrument. For a heating element such as that described in Shaw U.S. Pat. No. 4,185,632, or the above-incorporated U.S. patent application Ser. No. 07/986,967, filed Dec. 8, 1992, the method calls for monitoring the instantaneous current-voltage characteristics of the heating element to supply current levels that maintain the heating element temperature substantially near the auto-regulation temperature. Furthermore, the method of the present invention provides for calibrating the power supply to the power demand of the surgical instrument when it is connected to the power supply, and for shutting down supply of current to the heating element in the event that a fault or disconnect condition arises.

One skilled in the art will appreciate that the present invention can be practiced by other than the described embodiments, which are presented for purposes of illustration and not of limitation, and the present invention is limited only by the claims that follow.

What is claimed is:

1. Apparatus for performing surgery comprising:
a surgical instrument having a resistively-heated heating element;
a power supply for supplying an alternating current to the heating element, the power supply comprising:
a current supply circuit having a control terminal for accepting a control signal and having a first current supply circuit output terminal and a second current supply circuit output terminal for supplying the alternating current to the heating element coupled therebetween, the current supply circuit supplying the alternating current to the heating element in response to the control signal;

a current feedback circuit coupled between the second current supply circuit output terminal and the heating element for monitoring the alternating current as it is supplied by the current supply circuit, the current feedback circuit having a current feedback terminal for supplying a current feedback signal indicative of a magnitude of the alternating current as it is monitored by the current feedback circuit;

an error amplifier having a first error amplifier input for accepting a set-point signal, a second error amplifier input for accepting the current feedback signal, and an error amplifier output terminal for coupling the control signal, indicative of a difference between the set-point signal and the current feedback signal, to the control terminal of the current supply circuit, the error amplifier output terminal being coupled to the control terminal of the current supply circuit; and means for generating the set-point signal, the means for generating the set-point signal having a set-point output terminal coupled to the first error amplifier input, wherein the set-point signal is indicative of a predetermined magnitude of the alternating current corresponding to a predetermined heating element operating temperature and so that the alternating current supplied to the heating element is regulated to the predetermined magnitude set by the set-point generating means.

2. Apparatus for performing surgery as defined in claim 1 wherein the means for generating set-point signals further comprises:

a set-point indicator element disposed within the surgical instrument, the set-point indicator element having an impedance value indicative of a desired heating element operating temperature;

means for applying a voltage across the set-point indicator element;

means for measuring current through the set-point indicator element responsive to the voltage applied across the set-point indicator element; and means for selecting a set-point signal in response to the measured current to substantially maintain the heating element at the desired operating temperature.

3. Apparatus for performing surgery as defined in claim 2 wherein the set-point indicator element comprises a resistor having a resistance indicative of the desired heating element operating temperature.

4. Apparatus for performing surgery as defined in claim 1 wherein the surgical instrument further comprises a handle and a current step-up transformer disposed in the handle, and first and second leads, the current step-up transformer having a primary wire winding connected to the power supply and a secondary winding connected to the first and second electrical leads, the secondary winding comprising:

a washer having a periphery and a portion defining a centrally located aperture;

an inner tube having a central bore, first and second ends and an interior surface of the inner tube and an exterior surface of the inner tube, the washer affixed to the first end of the inner tube so that the central bore registers with the centrally located aperture of the washer;

an outer tube having a central bore, first and second ends, and interior and exterior surfaces, the washer affixed to the first end of the outer tube along its periphery, so that the washer, the exterior surface of the inner tube, and the interior surface of the outer tube form an assembly defining a closed-end annulus;

a plurality of magnetic toroids disposed in the closed-end annulus, each toroid being coated with an electrically insulating material;

a first terminal affixed to the interior surface of the inner tube; and a second terminal affixed to the exterior surface of the outer tube at a position diametrically opposing the first terminal, wherein the primary wire winding comprises a plurality of wire turns wrapped on the secondary winding so that each wire turn of the primary wire winding traverses the exterior surface of the outer tube, through the aperture in the washer, and along the inner surface of the inner tube, the plurality of primary wire turns having leads coupled to the power supply.

5. Apparatus for performing surgery as defined in claim 4 wherein the surgical instrument is coupled to the power supply by a cable so that the surgical instrument and cable present an impedance to the flow of alternating current, and wherein the current step-up transformer further comprises a series resonance capacitor disposed from the second terminal to match the electrical impedance of the surgical instrument to the power supply and cable to provide for efficient transmission of power therebetween.

6. Apparatus for performing surgery as defined in claim 1 wherein the current supply circuit further comprises:

an oscillator circuit that generates a high frequency signal of variable amplitude, the oscillator circuit having oscillator circuit input means and oscillator circuit output means, the oscillator circuit input means being the control terminal of the current supply circuit that is coupled to the error amplifier output terminal;

an oscillator buffer circuit that decouples and amplifies the high frequency signal, the oscillator buffer circuit having oscillator buffer circuit input means coupled to the oscillator circuit output means and the oscillator buffer circuit having oscillator buffer circuit output means; and a push-pull amplifier for further amplifying the decoupled and amplified high frequency signal, the push-pull amplifier having push-pull amplifier input means and push-pull amplifier output means, the push-pull amplifier input means being coupled to the oscillator buffer circuit output means, the push-pull amplifier output means being the first and second current supply circuit output terminals.

7. Apparatus for performing surgery as defined in claim 6 wherein the oscillator buffer circuit comprises:

an isolation buffer circuit for decoupling the oscillator circuit from the push-pull amplifier, the isolation buffer circuit having isolation buffer circuit input means coupled to the oscillator circuit output means and isolation buffer circuit output means; and a power buffer circuit for amplifying the current level of the oscillator circuit signal, the power buffer circuit having power buffer circuit input means coupled to the isolation buffer circuit output means and power buffer circuit output means coupled to the push-pull amplifier input means.

8. Apparatus for performing surgery as defined in claim 7 wherein the current feedback circuit further comprises:
   a current step-down transformer for providing a stepped-down current signal, the current step-down transformer having current step-down input means coupled to the push-pull amplifier output means and current step-down output means;
   a burden resistor for converting the stepped-down current signal supplied by the current step-down transformer to a corresponding voltage level signal, the burden resistor being coupled across the current step-down output means; and
   a converter circuit for converting the corresponding voltage level signal from an alternating current (AC) signal to a direct current (DC) signal, the converter circuit having converter circuit input means coupled across the burden resistor and converter circuit output means coupled to the second error amplifier input.

9. Apparatus for performing surgery as defined in claim 1 wherein the means for generating set-point signals further comprises:
   a microprocessor for establishing the set-point signal to substantially maintain the heating element at the operating temperature.

10. Apparatus for performing surgery as defined in claim 9 wherein:
   the material of the heating element further comprises a material that exhibits a Curie transition in permeability; and
   the operating temperature corresponds to an auto-regulation temperature.

11. Apparatus for performing surgery comprising:
   a surgical instrument having a resistively-heated heating element;
   a power supply for supplying an alternating current to the heating element, the power supply comprising:
      a current supply circuit having a control terminal for accepting a control signal and having a first current supply circuit output terminal and a second current supply circuit output terminal for supplying an alternating current to the heating element coupled therebetween, the current supply circuit supplying alternating current to the heating element in response to the control signal;
      a current feedback circuit coupled between the second current supply circuit output terminal and the heating element for monitoring the alternating current, the current feedback circuit having a current feedback terminal for supplying a current feedback signal indicative of a magnitude of the alternating current that is monitored by the current feedback circuit;
      an error amplifier having a first error amplifier input for accepting a set-point signal, a second error amplifier input for accepting the current feedback signal, and an error amplifier output terminal for coupling the control signal, indicative of a difference between the set-point signal and the current feedback signal, to the control terminal of the current supply circuit, the error amplifier output terminal being coupled to the control terminal of the current supply circuit; and
      means for generating the set-point signal, the means for generating the set-point signal having a set-point output terminal coupled to the first error amplifier input, wherein the set-point signal is indicative of a predetermined magnitude of alternating current corresponding to a predetermined heating element operating temperature and so that the alternating current supplied to the heating element is regulated to the predetermined magnitude set by the set-point generating means, wherein the means for generating set-point signals further comprises:
         a set-point indicator element disposed within the surgical instrument, the set-point indicator element having an impedance value indicative of a desired heating element operating temperature;
         means for applying a current across the set-point indicator element;
         means for measuring a voltage drop across the set-point indicator element responsive to the current applied across the set-point indicator element; and
         means for selecting a set-point signal in response to the measured voltage drop.

12. Apparatus for performing surgery as defined in claim 11 wherein the means for generating set-point signals comprises:
   a high frequency choke circuit for isolating the means for generating set-point signals from high frequency components of the alternating current in the surgical instrument, the high frequency choke circuit having high frequency choke circuit input means for coupling to a cable that in turn is coupled to the set-point indicator element and high frequency choke circuit output means;
   an analysis circuit for detecting a value of the set-point indicator element and supplying a set-point signal that corresponds to the value of the set-point indicator element, the analysis circuit having analysis circuit input means coupled to the high frequency choke circuit output means and analysis circuit output means; and
   an isolation buffer to prevent the feedback of high frequency signals from the current supply circuit from entering the analysis circuit, the isolation buffer having isolation buffer input means coupled to the analysis circuit output means and analysis circuit output means coupled to the second error amplifier input.

13. Apparatus for performing surgery comprising:
   a surgical instrument having a resistively-heated heating element;
   a power supply for supplying an alternating current to the heating element, the power supply comprising:
      a current supply circuit having a control terminal for accepting a control signal and having a first current supply circuit output terminal and a second current supply circuit output terminal for supplying an alternating current to the heating element coupled therebetween, the current supply circuit supplying alternating current to the heating element in response to the control signal;
      a current feedback circuit coupled between the second current supply circuit output terminal and the heating element for monitoring the alternating current, the current feedback circuit having a current feedback terminal for supplying a current feedback signal indicative of a magnitude of the alternating current that is monitored by the current feedback circuit;

an error amplifier having a first error amplifier input for accepting a set-point signal, a second error amplifier input for accepting the current feedback signal, and an error amplifier output terminal for coupling the control signal, indicative of a difference between the set-point signal and the current feedback signal, to the control terminal of the current supply circuit, the error amplifier output terminal being coupled to the control terminal of the current supply circuit; and means for generating the set-point signal, the means for generating the set-point signal having a set-point output terminal coupled to the first error amplifier input, wherein the set-point signal is indicative of a predetermined magnitude of alternating current corresponding to a predetermined heating element operating temperature and so that the alternating current supplied to the heating element is regulated to the predetermined magnitude set by the set-point generating means, wherein the means for generating set-point signals further comprises:

a set-point indicator element disposed within the surgical instrument, the set-point indicator element having an impedance value indicative of a desired heating element operating temperature;

means for applying a current across the set-point indicator element;

means for measuring a voltage drop across the set-point indicator element responsive to the current applied across the set-point indicator element; and means for selecting a set-point signal in response to the measured voltage drop, wherein the set-point indicator element comprises a resistor having a resistance indicative of the desired heating element operating temperature.

14. Apparatus for performing surgery comprising:
a surgical instrument having a resistively-heated heating element;
a power supply for supplying an alternating current to the heating element to substantially maintain the surgical instrument at a desired operating temperature, the power supply comprising:
a current supply circuit having a control terminal for accepting a control signal and having a first output terminal and a second output terminal for supplying the alternating current to the heating element coupled therebetween, the current supply circuit supplying the alternating current to the heating element in response to the control signal;
a current feedback circuit coupled between the second output terminal and the heating element for monitoring the alternating current as it is supplied by the current supply circuit, the current feedback circuit having a current feedback terminal for supplying a current feedback signal indicative of a magnitude of the alternating current as it is monitored by the current feedback circuit; and an error amplifier having a first input for accepting a set-point signal, a second input coupled to the current feedback terminal for accepting the current feedback signal, and an output terminal for coupling the control signal, indicative of the difference between the set-point signal and the current feedback signal, to the control terminal of the current supply circuit; and a circuit for generating the set-point signal wherein the set-point signal is indicative of a predetermined magnitude of the alternating current corresponding to a predetermined heating element operating temperature and so that the alternating current supplied to the heating element is regulated to the predetermined magnitude set by the set-point generating means to substantially maintain the heating element at the desired predetermined heating element operating temperature.

15. Apparatus for performing surgery as defined in claim 14 wherein the means for generating set-point signals further comprises:
a microprocessor for establishing the set-point signal to substantially maintain the heating element at the operating temperature.

16. Apparatus for performing surgery as defined in claim 15 wherein:
the heating element further comprises a material that exhibits a Curie transition in permeability; and
the operating temperature corresponds to an auto-regulation temperature.

17. Apparatus for performing surgery comprising:
a surgical instrument having a resistively-heated heating element;
a power supply for supplying an alternating current to the heating element to substantially maintain the surgical instrument at a desired operating temperature, the power supply comprising:
a current supply circuit having a control terminal for accepting a control signal and having a first output terminal and a second output terminal for supplying an alternating current to the heating element coupled therebetween, the current supply circuit supplying alternating current to the heating element in response to the control signal;
a current feedback circuit coupled between the second output terminal of the current supply circuit and the heating element for monitoring the alternating current, a monitored alternating current having a magnitude, the current feedback circuit having a current feedback terminal for supplying a current feedback signal indicative of the magnitude of the monitored alternating current;
an error amplifier having a first input for accepting a set-point signal, a second input coupled to the current feedback terminal for accepting the current feedback signal, and an output terminal for coupling the control signal, indicative of the difference between the set-point signal and the current feedback signal, to the control terminal of the current supply circuit; and
a circuit for generating the set-point signal wherein the set-point signal is indicative of a predetermined magnitude of alternating current corresponding to a predetermined heating element operating temperature and so that the alternating current supplied to the heating element is regulated to the predetermined magnitude set by the set-point generating means to substantially maintain the heating element at the desired predetermined heating element operating temperature, wherein the surgical instrument further comprises a handle and a current step-up transformer disposed in the handle, and first and second leads, the current step-up transformer having a primary wire winding connected to the power supply and a secondary winding connected to the first and second electrical leads, the secondary winding comprising:

a washer having a periphery and a portion defining a centrally located aperture;

an inner tube having a central bore, first and second ends and interior and exterior surfaces, the washer affixed to the first end of the inner tube so that the central bore registers with the centrally located aperture of the washer;

an outer tube having a central bore, first and second ends, and interior and exterior surfaces, the washer affixed to the first end of the outer tube along its periphery, so that the washer, the exterior surface of the inner tube, and the interior surface of the outer tube form an assembly defining a closed-end annulus;

a plurality of magnetic toroids disposed in the closed-end annulus, each toroid being coated with an electrically insulating material;

a first terminal affixed to the interior surface of the inner tube; and a second terminal affixed to the exterior surface of the outer tube at a position diametrically opposing the first terminal, wherein the primary wire winding comprises a plurality of wire turns wrapped on the secondary winding so that each wire turn of the primary wire winding traverses the exterior surface of the outer tube, through the aperture in the washer, and along the inner surface of the inner tube, the plurality of turns having leads coupled to the power supply.

* * * * *